United States Patent [19]

Noiles

[11] E Re. 28,895

[45] Reissued July 13, 1976

[54] ARTIFICIAL HIP JOINT

[75] Inventor: Douglas G. Noiles, New Canaan, Conn.

[73] Assignee: United States Surgical Corporation, Baltimore, Md.

[22] Filed: May 19, 1975

[21] Appl. No.: 579,006

Related U.S. Patent Documents

Reissue of:

[64] Patent No.: 3,848,272
Issued: Nov. 19, 1974
Appl. No.: 217,540
Filed: Jan. 13, 1972

[52] U.S. Cl. ..... 3/1.912; 3/1.913; 128/92 C; 128/92 CA

[51] Int. Cl.[2] ..... A61F 1/24

[58] Field of Search ..... 3/1, 1.9–1.913; 128/92 C, 92 CA, 92 R, 92 BA, 92 BB, 92 BC, 92 F, 92 G; 403/131, 140, 141, 143

[56] References Cited

UNITED STATES PATENTS

| | | | |
|---|---|---|---|
| 2,620,792 | 12/1952 | Cordasco | 128/92 BC |
| 2,696,817 | 12/1954 | Prevo | 128/92 C |
| 2,834,342 | 5/1958 | Yost | 128/92 BA |
| 3,067,740 | 12/1962 | Haboush | 128/92 CA |
| 3,269,758 | 8/1966 | Ulderup et al. | 403/131 X |
| 3,656,184 | 4/1972 | Chambers | 3/1.91 |
| 3,820,167 | 6/1974 | Sivash | 3/1.912 |

FOREIGN PATENTS OR APPLICATIONS

| | | | |
|---|---|---|---|
| 109,415 | 12/1939 | Australia | 128/92 C |
| 1,047,640 | 7/1953 | France | 128/92 C |
| 163,476 | 6/1958 | Sweden | 128/92 C |
| 162,762 | 4/1958 | Sweden | 128/92 CA |
| 459,462 | 9/1968 | Switzerland | 128/92 C |
| 1,215,737 | 12/1970 | United Kingdom | 128/92 C |

OTHER PUBLICATIONS

"Factors in the Design of an Artificial Hip Joint," by J. Charnley, The Institute of Mechanical Engineers, Proceedings, 1966–1967, vol. 181, Part 3J, pp. 108–111 relied upon.

"A Femoral-Head Prosthesis for the Hip Joint," by E. D. McBride, The Journal of Bone & Joint Surgery, vol. 32-A, No. 4, Oct. 1952, pp. 989–995.

*Primary Examiner*—Ronald L. Frinks
*Attorney, Agent, or Firm*—Fleit & Jacobson

[57] ABSTRACT

An artificial hip joint having an acetabulum prosthesis for the cotyloid cavity defining a socket and including a head having a plurality of blades extending outwardly away from the socket for engaging the prepared wall of the cotyloid cavity and having at least one insert removably connected to the head to form the socket. A prosthesis of the head of the femur is movably interconnected with the acetabulum prosthesis and includes a pin to be driven into the bone-marrow channel of the femur, a curved neck integral with the pin, and a hip ball positioned on the neck, movably located within the socket and in movable contact with the removable insert. Means are provided in operative relationship with the femur head prosthesis for preventing rotation of the femur head prosthesis with respect to the femur.

24 Claims, 22 Drawing Figures

ARTIFICIAL HIP JOINT

Matter enclosed in heavy brackets [ ] appears in the original patent but forms no part of this reissue specification; matter printed in italics indicates the additions made by reissue.

The present invention relates to artificial joints and more particularly to an artificial hip joint.

Numerous types of artificial hip joints have been developed and used. One successful example of such an artificial hip joint is that described in U.S. Pat. application Ser. No. 189,261 filed Oct. 14, 1971, *now U.S. Pat. No. 3,820,167* as a continuation-in-part of U.S. Pat. application Ser. No. 737,910, filed June 18, 1968, now abandoned.

Previously used hip joint prostheses have been made with various types of materials in attempts to provide both a strong joint and one that will not be unduly corroded by the body environment. Various styles and arrangements of hip joints having an artificial acetabulum articulately connected to an artificial caput femoris have been developed; however, use of some of these joints has made evident inherent disadvantages due to the shapes of the hips and because of the materials used. Frequently, bone growth stimulated as a result of mechanical irritation by the artificial joints has resulted in partial immobilization of the joints with a concomitant gradual increase of painful sensations.

Experience has also shown that it may often be desirable, due to wear or malfunction of the artificial hip joint, to replace the bearing surfaces of the joint after some period of use by the patient. In the past, however, it has not been possible to remove and replace the bearing surfaces from the implanted hip and the patient has thus been required to endure use of a poorly functioning artificial hip or has been required to undergo the procedures necessary for the complete replacement of the entire artificial hip joint.

Accordingly, it is an object of the present invention to provide an artificial hip joint that will have all of the functions inherent in a normal human hip joint and which possesses great strength and long service life.

Another object is to provide an artificial hip joint that is light in weight.

A further object of the invention is the provision of an artificial hip joint, portions of which can be replaced even after implantation in the patient.

Still another object of the present invention is the provision of an artificial hip joint that is relatively simple and inexpensive to manufacture and which is relatively easy to insert into the body.

Another object is to provide an artificial hip joint that is provided with means for preventing rotation of the femur head prosthesis with respect to the femur.

Additional objects and advantages of the invention will be set forth in part in the description which follows and in part will be obvious from the description, or may be learned by practice of the invention. The objectives and advantages are realized and attained by the instrumentalities and combinations particularly pointed out in the appended claims.

To achieve these and other objects, the present invention provides an artificial hip joint having an acetabulum prosthesis of the cotyloid cavity defining a socket and including a head, a plurality of blades extending outwardly away from the socket for engaging the prepared wall of the cotylōid cavity and further including at least one insert removably connected to the head to form the socket. A prosthesis of the head of the femur is movably interconnected with the acetabulum prosthesis and includes a pin to be driven into the bone-marrow channel of the femur, a curved neck integral with the pin and a hip ball positioned on the neck, movably located within the socket and in movable contact with the insert.

As here embodied, the acetabulum prosthesis head has a channel therein and the insert has a groove therein the groove and the channel being positioned in communicating relationship with respect to one another when the insert is positioned in connecting relationship with the acetabulum prosthesis head. In addition, a flexible ring member is positioned within the groove and within the channel to retain the insert in position within the acetabulum prosthesis head.

The acetabulum prosthesis head preferably has an entry slot therein in communication with the channel and the insert preferably has an entry passage therein in communication with the groove for enabling the ring to be inserted through the entry slot, and the entry passage and into the insert groove and the acetabulum prosthesis channel.

In a preferred embodiment, the insert further defines an extension well in communication with the entry passage for facilitating insertion and removal of the flexible ring. As here embodied, the artificial hip joint also preferably includes means in operative relationship with the femur head prosthesis for preventing rotation of the femur head prosthesis with respect to the femur.

It is to be understood, of course, that both the foregoing general description and the following detailed description are explanatory only and are not restrictive of the invention.

The accompanying drawings, which are incorporated in and constitute part of the specification, illustrate the invention and together with the description, serve to explain the principles of the invention.

Figure 1:
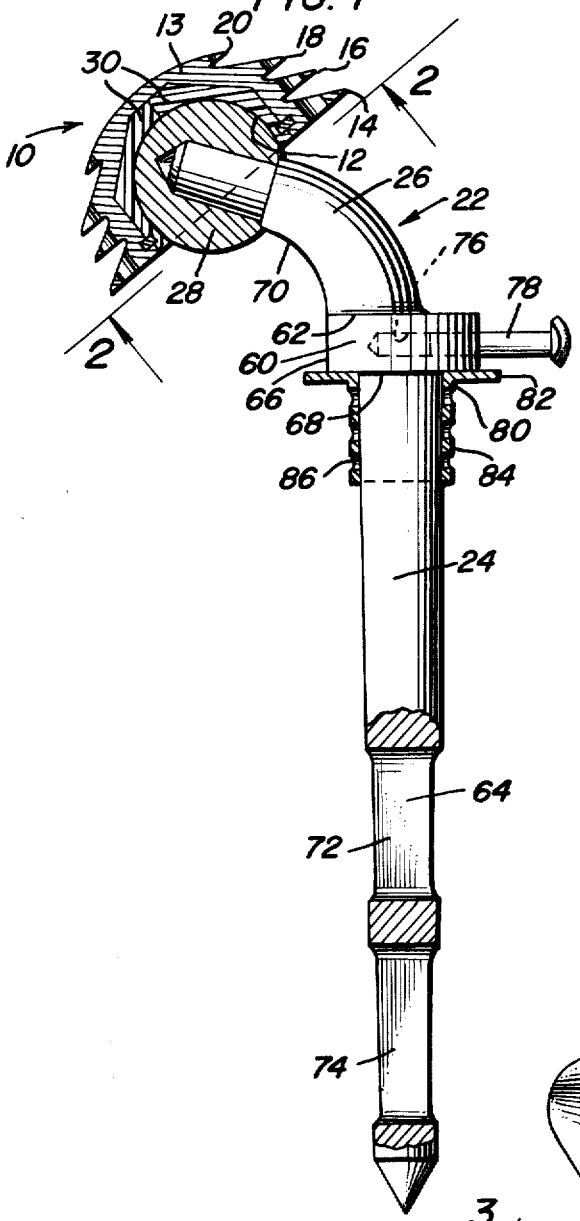
FIG. 1 is an elevation view, partly in section of one embodiment of the artificial hip joint of this invention.

With reference now to the drawings, wherein like reference characters designate like or corresponding parts throughout the several views, there is shown a machined acetabulum prosthesis 10 of the cotyloid cavity defining a socket 12 and including a head 13. A plurality of blades 14, 16, 18 and 20 extend outwardly away from the socket for engaging the prepared wall (not shown) of the cotyloid cavity.

A machined prosthesis 22 of the head of the femur is movably interconnected with the acetabulum prosthesis 10 and includes a pin 24 to be driven into the bone-marrow channel of the femur (not shown), a curved neck 26 integral with pin 24, and a hip ball 28 positioned on the neck and movably located within socket 12.

As here embodied, acetabulum prosthesis 10 includes at least one but preferably two inserts 30 removably connected to head 13 to form socket 12. The total area of the inserts forming the socket and bearing against hip ball 28 is more than one-half the spherical surface of the hip ball in order to retain the hip ball in position in the socket and to prevent the possibility of postoperative dislocation. The acetabulum prosthesis also has a plurality of blades 14, 16, 18 and 20 with notches and holes therein as described in pending U.S. Pat. application Ser. No. 189,261 filed Oct. 14, 1971.

The insert or plurality of inserts 30 are connected to head 13, and may be connected in a removable or in a permanent condition as will be explained more fully later in this specification.

Prosthesis 22 of the head of the femur, in addition to pin 24 and neck 26, also preferably includes an enlarged shoulder 60 integral with and positioned between the pin and the neck, and the neck is preferably formed with a base 62 joined to the shoulder and eccentrically positioned with respect to the central axis 64 of the pin. Shoulder 60 defines a side portion 66 and a lower surface 68, and it is surface 68 that rests on the upper portion of the severed femur when the artificial hip joint is installed. In a preferred construction of the artificial hip joint, an innermost portion 70 of the neck also extends in a continuous manner from side portion 66 of the shoulder.

It is also preferable and the preferred embodiment illustrated provides for a curvature of neck 26 so as to form an angle of substantially 120° with pin axis 64. The angle is measured between the pin axis and an imaginary line passing from the pin axis through the center of hip ball 28 and tangentially to the innermost curved surface 70 of the neck.

Pin 24 also defines two slots 72 and 74 opening in directions parallel to the direction of curvature of neck 26. The function of these slots is similar to the function of the holes in prosthesis 10, and slots 72 and 74 permit bone tissue to row therethrough so as to fix pin 24 and prosthesis 22 within the femur. Pin 24 is also tapered away from neck 26, and the neck is tapered away from the pin. The taper of the pin permits it to be driven downwardly and into the bone-marrow channel of the femur.

In an alternative arrangement and use of the artificial hip joint of this invention, shoulder 60 is provided with a hole 76 entering the side portion 66 of the shoulder. A rod 78 is also provided, and it is adapted to pass through a hole drilled in the greater trochanter (not shown) and to be driven into hole 76 to hold the greater trochanter in proper position after the artificial joint has been installed.

In another embodiment and use of the hip joint, a collar 80 is provided for insertion into the upper part of the femur and for providing additional support for the artificial hip on the femur when necessary. The collar is provided with a flange portion 82 for engaging the lower surface 68 of shoulder 60, and the collar is also provided with a sleeve portion 84 integral with flange portion 82 for sliding over pin 24 so that the collar can be positioned on the upper part of the severed femur. Pin 24 can, thus, be inserted through the collar and into the bone-marrow channel of the femur to cause shoulder 60 to rest on flange portion 82.

It is also preferable that sleeve portion 84 of the collar be provided with a plurality of holes 86 for enabling bone tissue to grow through the holes and to assist in holding the collar in its proper position on the femur.

As previously mentioned, inserts 30 are preferably removably connected to head 13. This is particularly desirable since it readily facilitates replacement of the inserts if they become worn or otherwise damaged after a period of use in the body of the patient.

In a preferred embodiment, acetabulum prosthesis head 13 has a channel 88 therein and the insert or inserts 30 has a groove or grooves 90 therein. The channel and the grooves are so positioned with regard to the dimensions of head 13 and inserts 30 that when groove 90 and channel 88 are positioned in communicating relationship with respect to one another the inserts are tightly positioned and engage the inner portion of head 13. A flexible ring member 92 is normally positioned within groove 90 and within channel 88 to retain the insert or inserts 30 in position with acetabulum prosthesis head 13.

In order to facilitate insertion and removal of flexible ring 92, acetabulum prosthesis head 13 is provided with an entry slot 94 located in communication with channel 88 and at least one insert 30 is provided with an entry passage 96 in communication with groove 90. Both entry slot 94 and entry passage 96 are readily accessible for enabling the ring to be inserted into the groove and the channel or to facilitate removal of the ring when removal of inserts 30 is desired.

Entry slot 94 and entry passage 96 are preferably formed to each subtend an angle of substantially 25°, wherein the vertex of the angle is located at the center of hip ball 28. This provides the necessary space for enabling easy insertion and removal of ring member 92. In addition, channel 88 and groove 90 are dimensioned such that ring member 92, when in its inserted position, bears primarily against a lower surface 98 of channel 88 and against an upper surface 100 of groove 90 so as to force inserts 30 into tight-fitting contact with acetabulum prosthesis head 13 along adjoining surfaces 102 and 104, for example.

Flexible ring 92 is preferably non-continuous and may be provided with an enlarged end and an aperture 106 at one or both ends to facilitate grasping of the ring by a tool (not shown) and to prevent rotation of the ring within the channel and the groove so that the aperture 106 is always accessible. In order to further facilitate grasping of the ring member for insertion and removal thereof, insert 30 preferably defines an extension well 108 in communication with entry passage 96 and with groove 90. This well enables a tool to be inserted through ring aperture 106 and permits the tool to extend into extension well 108 during the removal or insertion procedure.

Although not illustrated, an entry slot and an entry passage similar and in addition to slot 94 and to passage 96 can be provided in head 13 and in inserts 30, respectively, and located at a different location from slot 94 and passage 96. In this embodiment, two rings are provided instead of one and each ring extends substantially half way around channel 88 and groove 90. Each ring can then be inserted and removed via its respective entry passage and entry slot.

The artificial hip joint of the present invention is preferably constituted of surgical grade materials suitable for implantation into the body.

It is desirable to use titanium or a titanium alloy for the greater portion of the artificial hip joint because this has proven to be highly effective in providing the desired strength while also providing for the desired resistance to corrosion. It may be desirable to use a cobalt alloy for the hip ball 28 and for inserts 30. However, it may also be desirable for economic and other reasons to use a plastic material for inserts 30, such as an ultra high molecular weight polyethylene. The use of such a plastic material for the inserts may permit the use of titanium or a titanium alloy for the hip ball, and the artificial hip joint can be made lighter in weight as a result.

In one embodiment, for example, the entire artificial hip joint with the exception of inserts 30 may be comprised of titanium or a titanium alloy and the titanium may be, for example, ASTM F67–66 and the titanium alloy may be, for example, ASTM F 136–70, where collar 80 and rod 78 are utilized, these elements may also be comprised of the same titanium or titanium alloy that is used in the remaining portions of the joint. Similarly, flexible ring member or members 92 may also be made of the same titanium or titanium alloy that is used in the remaining portions of the joint.

Another embodiment of the invention, however, utilizes the same titanium or titanium alloy for all portions of the joint with the exception of hip ball 28 and inserts 30. In this embodiment, the hip ball and inserts may each be comprised of cobalt alloy ASTM F75–67, as an example.

Figure 6:
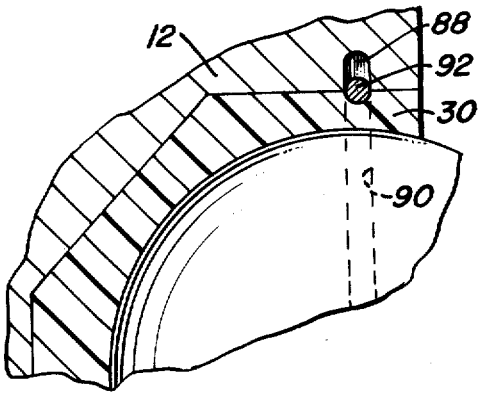
FIG. 6 is a fragmentary sectional view of still another embodiment of the invention for holding the inserts in position.
Figure 5:
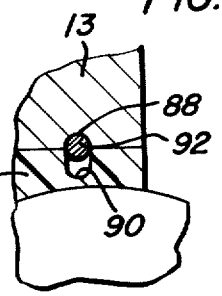
FIG. 5 is a fragmentary sectional view of another embodiment of the invention for holding the inserts in position.

In another embodiment of the invention wherein the inserts are permanently positioned within acetabulum prosthesis head 13, (FIG. 5) head 13 is provided with channel 88 and inserts 30 are provided with grooves 90. When assembled, channel 88 and grooves 90 are positioned in communication with each other and a ring member 92, which need not have an aperture therein, is positioned within the channel and within the grooves for retaining inserts 30 in position within acetabulum prothesis head 13. The ring is preferably flexible so as to spring into channel 88 from groove 90 when inserts 30 are properly positioned within the head 13. Conversely, the ring may be initially expanded (FIG. 6) within channel 88 so as to spring into grooves 90 when the channel and the grooves are positioned in communication with one another.

When using an artificial hip joint, it is extremely important that the artificial joint be rigidly held with respect to the femur so that it does not rotate relative to the femur. In order to firmly fix the artificial hip joint with respect to the femur, the present invention provides means in operative relationship with the femur head prosthesis for preventing rotation of the femur head prosthesis with respect to the femur.

Figure 7:
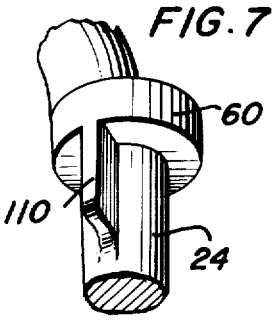
FIG. 7 is a fragmentary perspective view of one anti-rotation embodiment of the invention.

As here embodied, and as illustrated in FIG. 7, the rotation, preventing means includes a fin member 110 integral with and extending from pin 24 for engaging a slot (not shown) cut into the femur by the surgeon. Fin 110 preferably extends only along a small portion of pin 24 and the fin is positioned within the slot to prevent rotation of pin 24 within the bone-marrow channel of the femur.

Figure 8:
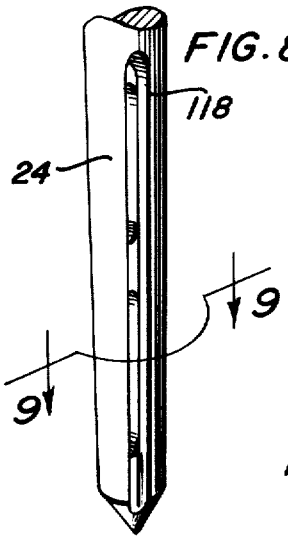
FIG. 8 is a fragmentary perspective view of another anti-rotation embodiment.
Figure 9:
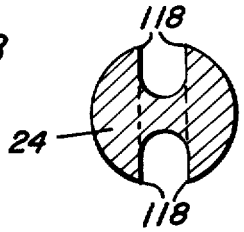
FIG. 9 is a sectional view taken on the line 9—9 of FIG. 8 and looking in the direction of the arrows.

Another anti-rotation embodiment of the artificial hip joint is illustrated in FIGS. 8 and 9, wherein the rotation preventing means includes a plurality of knife edges 118 integral with and extending longitudinally along pin 24 for cutting into the femur so as to prevent rotation of the femur head prosthesis relative to the femur.

Figure 10:
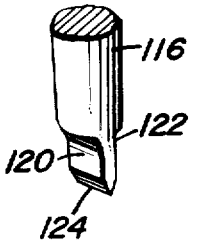
FIG. 10 is a fragmentary view of another anti-rotational embodiment of the invention.
Figure 11:
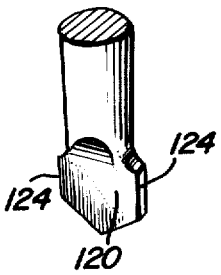
FIG. 11 is a fragmentary view of still another anti-rotation embodiment.

An alternative anti-rotation feature is illustrated in FIG. 10, wherein a sharpened spade end 120 extends from the end of pin 24 to be driven into the bone-marrow channel 114 of femur 116 beyond a reamed portion 122 within the bone-marrow channel. The spade end may also include blades 124 (FIG. 11) integral with the spade for engaging the femur and for preventing rotation of pin 24 relative to the femur.

Figure 12:
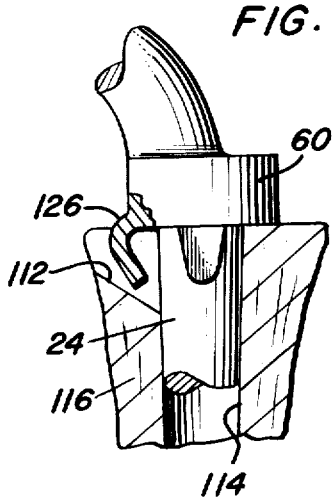
FIG. 12 is a fragmentary view, partly in section, of an alternative anti-rotation embodiment for preventing rotation of the femur head prosthesis with respect to the femur.

Additional embodiments of the anti-rotation feature of the invention are illustrated in FIGS. 12–17. As shown in FIG. 12, shoulder 60 is provided with a key 126 connected thereto and extending outwardly and downwardly from the shoulder for fitting into cut-out portion or slot 112 in the femur. Where collar 80 is utilized (FIG. 13), a keyway 128 is provided in the collar to receive key 126 and to assist in preventing rotation of pin 24 relative to the femur.

In a further anti-rotation embodiment (FIG. 14), shoulder 60 has an aperture 130 therein and a square headed pin 132 or other shaped pin having a head to bear against the sides of femur slot 112 is positioned within aperture 130 and extends outwardly and downwardly from shoulder 60 for positioning within femur slot 112 and to prevent rotation of pin 24 within the femur.

Figure 15:
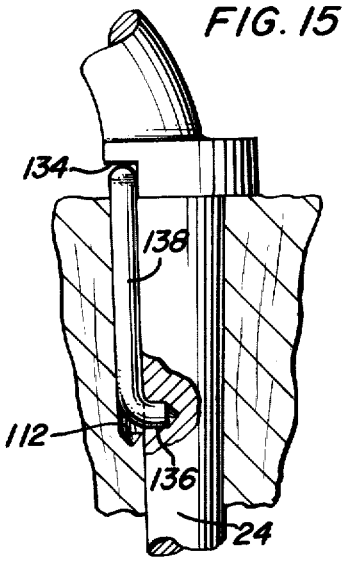
FIG. 15 is a fragmentary view, partly in section, of a further anti-rotation feature of the invention.
Figure 14:
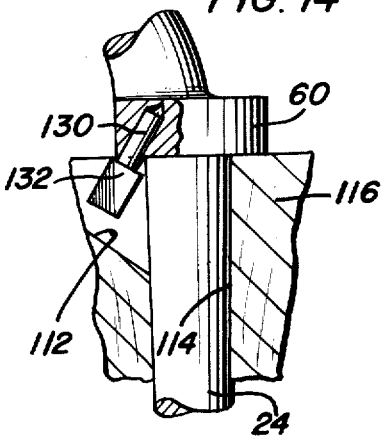
FIG. 14 is a fragmentary view, partly in section, of still another anti-rotation embodiment.
Figure 13:
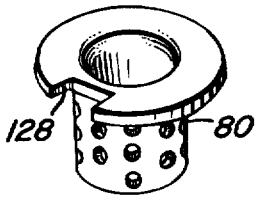
FIG. 13 is a perspective view of a collar for use with the embodiment illustrated in FIG. 12.

Rotation of pin 24 within the femur may also be prevented by means of the embodiment illustrated in FIG. 15. In this arrangement, shoulder 60 is provided with a cavity 134 and pin 24 is provded with an aperure 136. A rod 138 is positioned within shoulder cavity 34 at one end and is located along pin 24 with a second end of the rod positioned within pin aperture 136. A femur slot 112 is again cut into the femur for receiving rod 138, and this prevents rotation of pin 24 within the femur.

Figure 16:
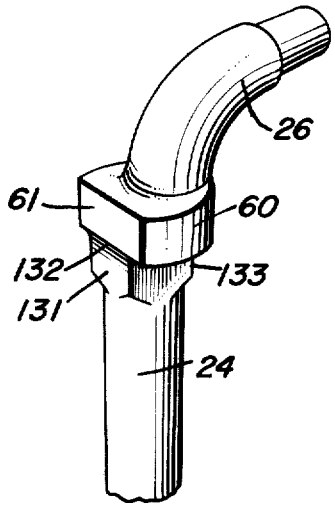
FIG. 16 is a fragmentary view of an additional anti-rotation embodiment.

An additional anti-rotation feature of this invention is illustrated in FIG. 16 wherein a member 131 defining a plurality of corners 133 is integral with the pin and immediately below shoulders 60. Member 131 is preferably substantially square in cross section and corners 133 preferably extend substantially parallel with the axis of pin 24.

The dimensions of the cross-section of square member 131 may be such that the length of each side of the square is equal to the diameter of pin 24 adjacent to shoulder 60. Alternatively, the sides of square member 131 may be larger than the diameter of pin 24.

Figure 17:
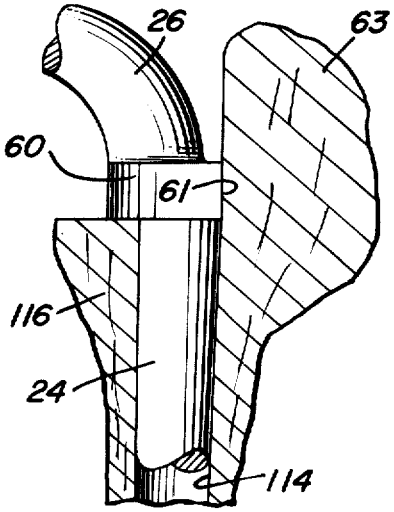
FIG. 17 illustrates a further embodiment of the invention.

In performing the operation of inserting the artificial hip joint of this invention, it may frequently be desirable to avoid completely severing the greater trochanter. Accordingly, it may be desirable, for this reason, to form shoulder 60 with a flattened side 61, as illustrated in FIGS. 16 and 17 whereby the flattened side can be positioned in abutting relationship with the greater trochanter 63. This positioning of shoulder 60 and of flattened side 61 flush with the greater trochanter, of course, also prevents rotation of the femur head prosthesis with respect to the femur, and the anti-rotation feature of flattened side 61 is also enhanced by the fact that side 61 is preferably oriented substantially parallel with the axis pin 24. It is, of course, within the scope of this invention to provide for a prosthesis as described, but having flattened side 61 without the use of member 131 or to provide for a prosthesis as described but having member 131 without flattened side 61 or shoulder 60.

Figure 18:
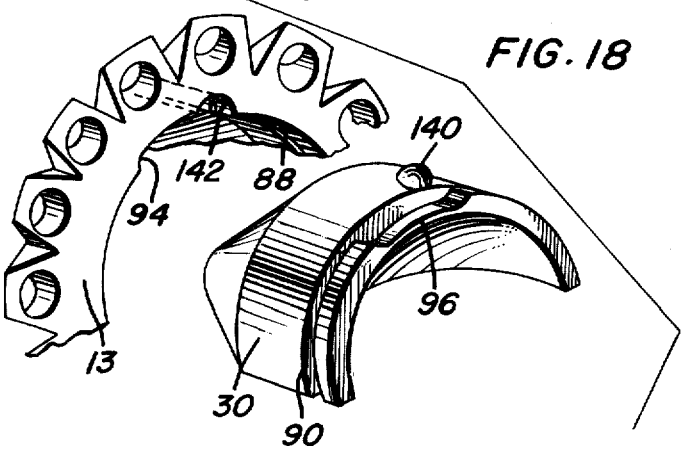
FIG. 18 is a fragmentary exploded perspective view of an embodiment of the invention for preventing rotation of the inserts within the acetabulum prosthesis.

Another embodiment of the invention designed to prevent relative movement or rotation between inserts 30 and acetabulum prosthesis head 13 is illustrated in FIG. 18. Prevention of rotation between inserts 30 and acetabulum prosthesis head 13 is important because the hip is designed for relative movement between inserts 30 and hip ball 28. The hip ball and the inserts are specifically designed for this purpose and are made of materials to withstand frictional movements therebetween. However, acetabulum prosthesis head 13 and inserts 30 are not so designed and relative movement between head 13 and inserts 30 is to be avoided. In addition, it is desirable to maintain entry slot 94 and entry passage 96 aligned so that it is always possible to insert or remove flexible ring member 92. Of course, if entry slot 94 and entry passage 96 were permitted to move relative to one another, it would not be possible to insert or remove the flexible ring member until entry slot 94 and entry passage 96 were realigned.

Figure 3:
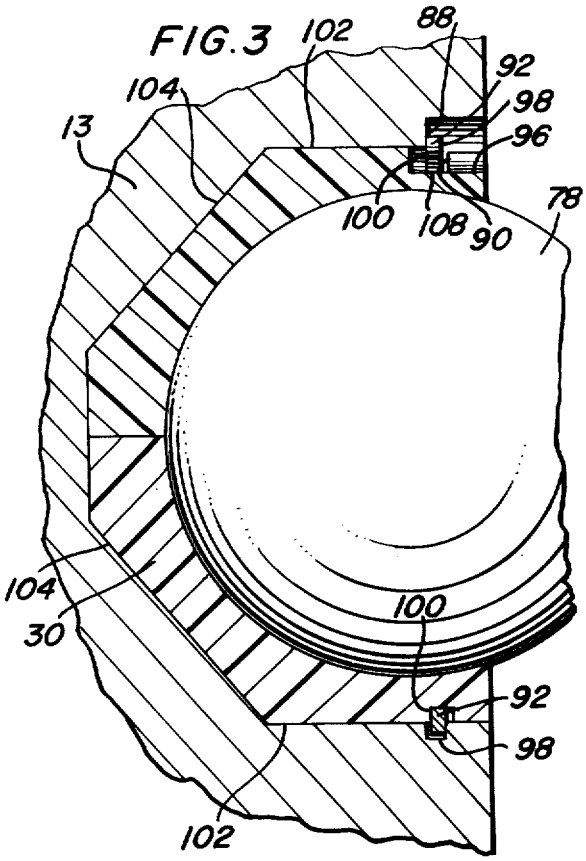
FIG. 3 is a view taken on the line 3—3 of FIG. 2 and looking in the direction of the arrows.
Figure 4:
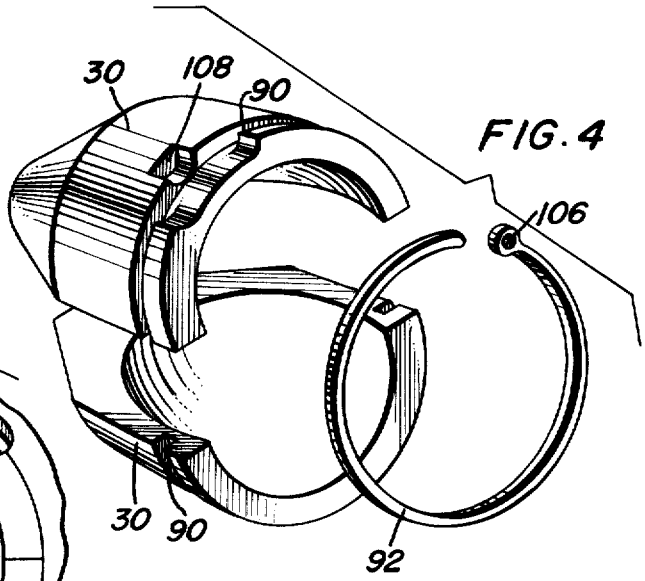
FIG. 4 is an exploded perspective view of one embodiment of the acetabulum prosthesis head inserts and of the flexible ring member used to hold the inserts in place.
Figure 2:
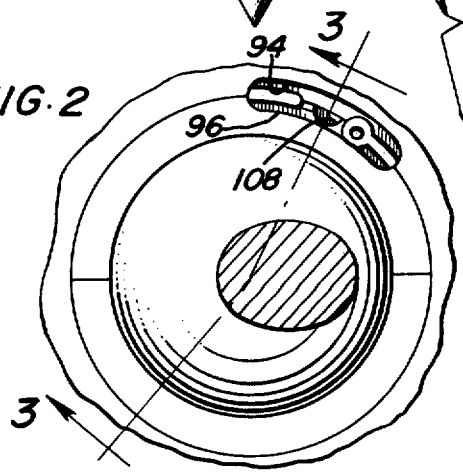
FIG. 2 is a view taken on the line 2—2 of FIG. 1 and looking in the direction of the arrows.

Therefore, one embodiment of this invention provides for a projection 140 on at least one of inserts 30, and acetabulum prosthesis head 13 is formed with a depression 142 therein for receiving projection 140 so as to prevent relative movement of inserts 30 with respect to head 13. If desired, depression 142 can be so positioned that it also acts in the manner of extension well 108 in the embodiment of FIGS. 2–4 to permit the entry of a tool for grasping flexible ring member 92.

As previously explained, experience has shown that it may often be desirable, due to wear or malfunction of the artificial hip joint, to repair or replace the bearing surfaces of the joint after some period of use by the patient. For this reason, this invention provides for the easy removal of inserts 30 from the artificial hip joint. However, if the bearing surfaces of the joint require replacement or repair after some period of use by the patient, it may be desirable to remove and replace hip ball 28, and this removable feature is illustrated in FIGS. 19 and 20.

Figure 19:
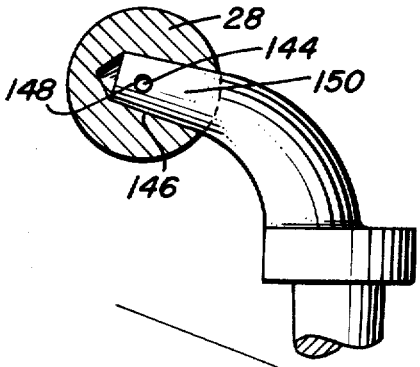
FIG. 19 is a fragmentary view of a feature of the invention providing for removal of the hip ball.

As illustrated in FIG. 19, hip ball 28 is removably positioned on curved neck 26, and the hip ball is provided with an aperture 144 therein. Neck 26 is also provided with an aperture 146 in alignment with hip ball aperture 144, and a holding pin 148 extends through apertures 144 and 146 for holding hip ball 28 on neck 26. Holding pin 148 is frictionally and tightly held within apertures 144 and 146 so that hip ball 28 is firmly and fixedly held on to neck 26 during use of the artificial hip joint. However, when it is desired to remove hip ball 28 from the neck, pin 148 may be hammered out from apertures 144 and 146 to facilitate repair of the hip ball or replacement thereof.

Figure 20:
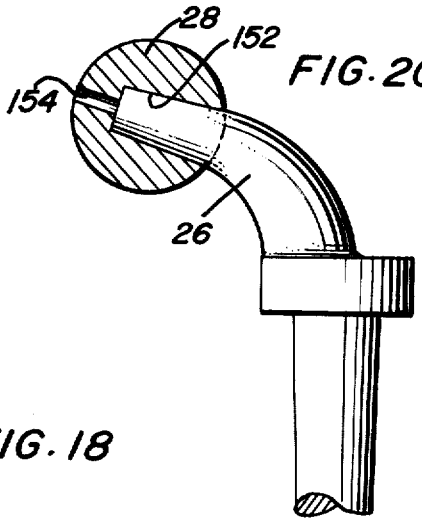
FIG. 20 is a fragmentary view of another embodiment permitting removal of the hip ball.

An alternative embodiment of removable hip ball 28 is illustrated in FIG. 20 wherein neck 26 is provided with a free and tapered end 150. Hip ball 28 is provided with a tapered opening 152 for tightly engaging tapered end 150 of the neck. Thus, the hip ball can be pressed onto the tapered end 150 of neck 26 to be firmly held in position. Hip ball 28, however, is also provided with a hole 154 extending between the exterior surface of the hip ball and in communication with tapered opening 152 within the hip ball for facilitating removal of the hip ball from the neck by conventional tools (not shown).

Figure 21:
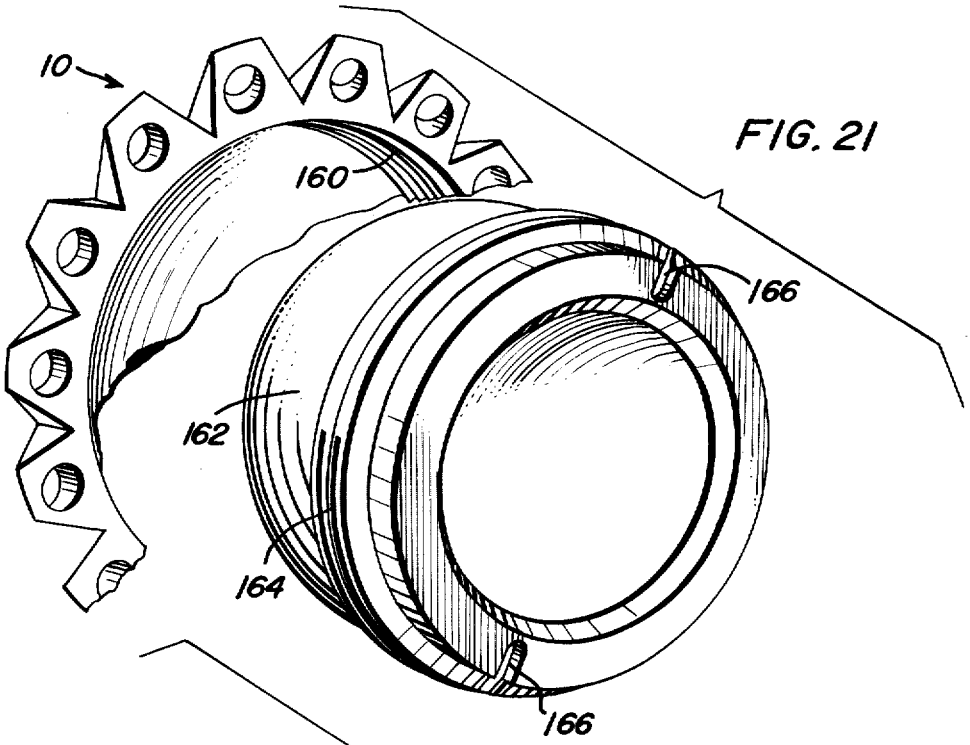
FIG. 21 is a fragmentary perspective view of an additional embodiment of the invention.

A further embodiment of the artificial hip joint, and particularly the insert, is illustrated in FIG. 21. In this embodiment, acetabulum prosthesis 10 is provided with threaded grooves 160. Insert 162 is formed of one single piece and includes an integral threaded ring portion 164 for threadedly engaging acetabulum prosthesis grooves 160. Insert 162 further defines notches 166 adjacent to threaded ring 164 for enabling the insert to be screwed into position with the ring threadedly engaging grooves 160.

As in the previous embodiments, the insert socket 12 defines more than a hemisphere so that the hip ball is retained within the socket to prevent postoperative separation.

The insert illustrated in FIG. 21 is preferably comprised of plastic, such as ultra high molecular weight polyethylene. The plastic is initially heated to cause expansion, and hip ball 28 is then popped into socket 12. The insert is then allowed to cool so that it contracts around the hip ball, and the insert with the hip ball therein is then screwed into acetabulum prosthesis 10 by means of threaded ring 164 and grooves 160 until the insert is tightly positioned within the acetabulum prosthesis.

If desired, and where insert 162 is comprised of metal, insert 162 is preferably formed as two pieces. This embodiment is illustrated in FIG. 22, and the insert in this embodiment is preferably comprised of cobalt alloy, such as ASTM F75–67.

Figure 22:
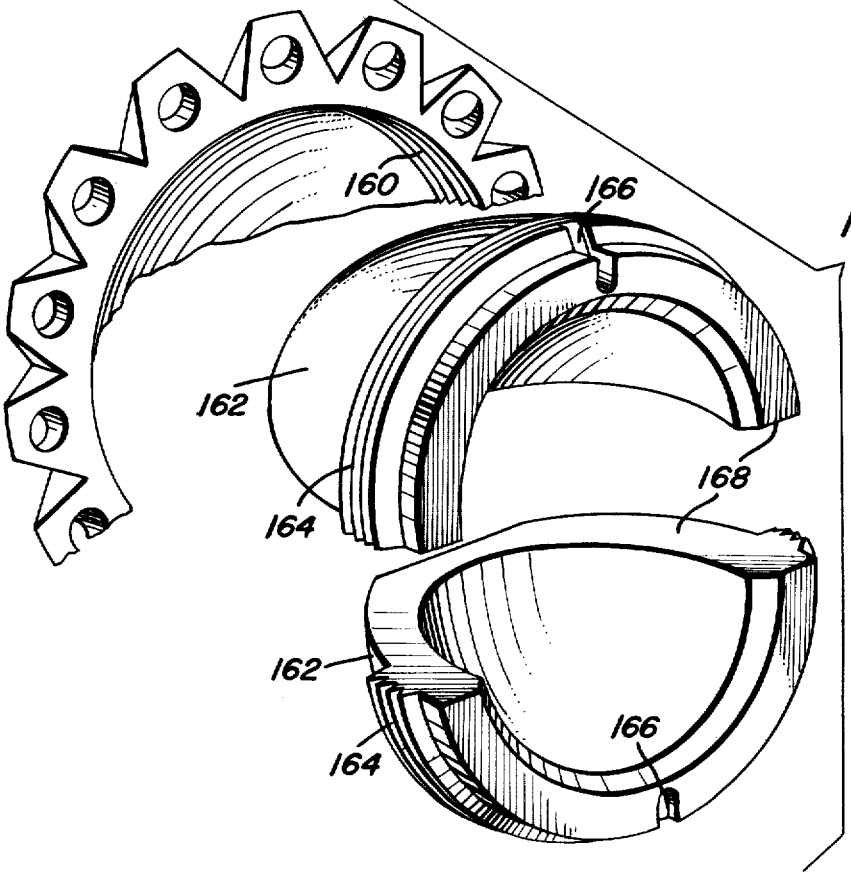
FIG. 22 is a fragmentary perspective view of a further embodiment of the invention.

In assembling the embodiment illustrated in FIG. 22, the two pieces of insert 162 are first positioned around hip ball 28. The pieces of the insert are formed so that faces 168 abut against one another in contiguous relationship. The assembly of the hip ball together with the two pieces of the insert is then screwed into acetabulum prothesis. 10 with threaded ring 164 engaging grooves 160.

The embodiments described and illustrated in FIGS. 21 and 22 are particularly advantageous. The unitary construction of the inserts renders the hip extremely rugged and permits it to withstand large forces and stresses. Additionally, the threaded grooves within the acetabulum prosthesis and the threaded ring integral with the insert permit the insert to be readily removed from the acetabulum prosthesis in the event that the insert needs to be replaced or repaired. This, of course can be done even after the hip has been inserted in the patient.

The present invention, thus provides for an extremely versatile and durable artificial hip joint that is inexpensive to manufacture and which is designed to facilitate easy replacement of bearing surface portions of the artificial hip joint, if and when such replacement becomes necessary or desirable. The artificial hip joint of this invention also provides for novel anti-rotation means that act in conjunction with the femur to prevent rotation of the artificial hip joint relative to the femur. This, of course, is extremely important for the successful use of the hip joint and this anti-rotation feature also permits the patient to quickly gain the full use of the hip joint after insertion of the hip joint.

The invention in its broader aspects is not limited to the specific details described, and departures may be made from such details without departing from the principles of the invention and without sacrificing its chief advantages.

What is claimed is:

1. An artificial hip joint, comprising: an acetabulum prosthesis of the cotyloid cavity defining an aperture having screw threads on the inner surface thereof and a plurality of blades extending outwardly away from siad aperture for engaging the prepared wall of the cotyloid cavity;

at least one insert having an outer threaded surface and an inner bearing surface inserted into said aperture and threadedly connected by means of said threads to said acetabulum prosthesis to form a socket, the outer surface of said at least one insert engaging and being supported by the inner surface of said aperture; and a prosthesis of the head of the femur movably interconnected with said acetabulum prosthesis and including a pin to be driven into the bone-marrow channel of the femur, a [ curved ] neck integral with the pin, and a hip ball positioned on the neck, movably located within said socket and in movable contact with said insert, said socket enveloping more than one-half of the hip ball to prevent withdrawal of the hip ball from the socket, said artificial hip joint composed of surgical grade materials suitable for implantation into the body.

2. An artificial hip joint as in claim 1 wherein said insert is comprised of plastic.

3. An artificial hip joint as in claim 1 wherein said acetabulum prosthesis includes two of said inserts.

4. An artificial hip joint as in claim 1 wherein said insert is comprised of ultra high molecular weight polyethylene.

5. An artificial hip joint as in claim 4 wherein said hip ball is comprised of titanium or a titanium alloy.

6. An artificial hip joint as in claim 1 wherein said insert is comprised of cobalt alloy ASTM F75–67.

7. An artificial hip joint as in claim 1 wherein said hip ball is comprised of cobalt alloy.

8. An artificial hip joint as in claim 1 wherein all of said acetabulum prosthesis but the insert and all of the prosthesis of the head of the femur but the hip ball are comprised of titanium or a titanium alloy.

9. An artificial hip joint as in claim 8 wherein the titanium alloy is ASTM F136–70.

10. An artificial hip joint as in claim 8 wherein the titanium is ASTM F67–66.

11. An artificial hip joint as in claim 1 wherein said insert includes an integral threaded ring portion for threadedly engaging grooves in said acetabulum prosthesis.

12. An artificial hip joint as in claim 11 wherein said insert further defines notches adjacent said threaded ring for enabling said insert to be screwed into position with said ring threadedly engaging said grooves.

13. An artificial hip joint as in claim 1 wherein said insert is formed as one unitary piece.

14. An artificial hip joint comprising: an acetabulum prosthesis of the cotyloid cavity defining an aperture having screw threads on the inner surface thereof;

at least one insert having an outer threaded surface and an inner bearing surface inserted into said aperture and threadedly connected by means of said threads to said acetabulum prosthesis to form a socket, the outer surface of said at least one inert engaging and being supported by the inner surface of said aperture; and a prosthesis of the head of the femur movably interconnected with said acetabulum prosthesis and including a pin to be driven into the bone-marrow channel of the femur, a [ curved ] neck integral with the pin, and a hip ball positioned on the neck, movably located within said socket and in movable contact with said insert, said socket enveloping more than one-half of the hip ball to prevent withdrawal of the hip ball from the socket, said artificial hip joint composed of surgical grade materials suitable for implantation into the body.

15. An artificial hip joint as in claim 14 wherein said insert includes an integral threaded ring portion for threadedly engaging said acetabulum prosthesis threads.

16. An artificial hip joint as in claim 15 wherein said insert further defines notches adjacent to said threaded ring for enabling said insert to be screwed into position with said ring threadedly engaging said threads.

17. An artificial hip joint as in claim 14 wherein said insert socket defines more than a hemisphere.

18. An artificial hip joint as in claim 14 wherein said insert is formed as one unitary piece.

19. An artificial hip joint as in claim 18 wherein said insert is comprised of plastic.

20. An artificial hip joint as in claim 19 wherein said plastic is ultra high molecular weight polyethylene.

21. An artificial hip joint as in claim 14 wherein said insert is formed as two pieces.

22. An artificial hip joint as in claim 21 wherein said insert is comprised of cobalt alloy.

23. An artificial hip joint as in claim 22 wherein said cobalt alloy is ASTM F75–67.

24. An artificial hip joint as in claim 14 further including means in operative relationship with said femur head prosthesis for preventing rotation of the femur head prosthesis with respect to the femur.

* * * * *